(12) United States Patent
Gammons

(10) Patent No.: US 7,291,163 B2
(45) Date of Patent: *Nov. 6, 2007

(54) INFLATABLE THERMAL BLANKET HAVING AIR FLOW CHANNELS FOR DIRECTING A CONDITIONED GAS

(75) Inventor: Clifford Eugene Gammons, Loudon, TN (US)

(73) Assignee: Adroit Development, Inc., Loudon, TN (US)

( * ) Notice: Subject to any disclaimer, the term of this patent is extended or adjusted under 35 U.S.C. 154(b) by 360 days.

This patent is subject to a terminal disclaimer.

(21) Appl. No.: 10/987,597

(22) Filed: Nov. 12, 2004

(65) Prior Publication Data

US 2005/0107856 A1    May 19, 2005

Related U.S. Application Data

(60) Provisional application No. 60/520,428, filed on Nov. 12, 2003.

(51) Int. Cl.
*A61F 7/00* (2006.01)

(52) U.S. Cl. .................... 607/104; 607/114

(58) Field of Classification Search ............ 607/96, 607/104, 108–102, 114
See application file for complete search history.

(56) References Cited

U.S. PATENT DOCUMENTS

| | | |
|---|---|---|
| 1,777,982 A | 10/1930 | Popp |
| 2,093,834 A | 9/1937 | Gaugler |
| 3,653,083 A | 4/1972 | Lapidus |
| 4,347,633 A | 9/1982 | Gammons et al. |
| 4,572,188 A | 2/1986 | Augustine et al. |
| 4,660,388 A | 4/1987 | Greene, Jr. |
| 4,777,802 A | 10/1988 | Feher |
| 5,106,373 A | 4/1992 | Augustine et al. |
| 5,165,400 A | 11/1992 | Berke |
| 5,184,612 A | 2/1993 | Augustine |
| 5,246,656 A | 9/1993 | Stephenson et al. |
| 5,300,101 A | 4/1994 | Augustine et al. |
| 5,300,102 A | 4/1994 | Augustine et al. |
| 5,304,213 A | 4/1994 | Berke et al. |
| 5,324,320 A | 6/1994 | Augustine et al. |
| 5,336,250 A | 8/1994 | Augustine |
| 5,350,417 A | 9/1994 | Augustine |
| 5,405,371 A | 4/1995 | Augustine et al. |
| 5,443,488 A * | 8/1995 | Namenye et al. ........... 607/104 |
| 5,545,194 A | 8/1996 | Augustine |
| 5,655,237 A | 8/1997 | Suzuki et al. |
| 5,674,269 A * | 10/1997 | Augustine ................... 607/107 |
| 5,824,025 A | 10/1998 | Augustine |
| 5,860,292 A | 1/1999 | Augustine et al. |

(Continued)

FOREIGN PATENT DOCUMENTS

GB    716746    10/1954

(Continued)

*Primary Examiner*—Roy D. Gibson
(74) *Attorney, Agent, or Firm*—Pitts & Brittian, PC

(57) ABSTRACT

An apparatus for providing conditioned air to a patient while maintaining a low profile over the patient. The therapy blanket has an inflatable portion that includes air channels with a constriction in the area where the blanket covers the torso of the patient; thereby reducing, if not eliminating, bunching of the blanket. The blanket covers the torso and at least one extended arm of a patient.

20 Claims, 3 Drawing Sheets

U.S. PATENT DOCUMENTS

| | | |
|---|---|---|
| 5,928,274 A | 7/1999 | Augustine |
| 5,989,285 A * | 11/1999 | DeVilbiss et al. .......... 607/107 |
| 6,102,936 A | 8/2000 | Augustine et al. |
| 6,176,870 B1 * | 1/2001 | Augustine ................... 607/107 |
| 6,203,567 B1 * | 3/2001 | Augustine ................... 607/104 |
| 6,210,428 B1 | 4/2001 | Augustine et al. |
| 6,228,107 B1 | 5/2001 | Arnold et al. |
| 6,487,871 B1 | 12/2002 | Augustine et al. |

FOREIGN PATENT DOCUMENTS

| | | |
|---|---|---|
| GB | 1334935 | 10/1973 |
| GB | 1556207 | 4/1980 |
| WO | PCT/US85/00071 | 8/1985 |

* cited by examiner

INFLATABLE THERMAL BLANKET HAVING AIR FLOW CHANNELS FOR DIRECTING A CONDITIONED GAS

CROSS-REFERENCE TO RELATED APPLICATIONS

This application claims the benefit of U.S. Provisional Application No. 60/520,428, filed Nov. 12, 2003.

STATEMENT REGARDING FEDERALLY SPONSORED RESEARCH OR DEVELOPMENT

Not Applicable

BACKGROUND OF THE INVENTION

1. Field of Invention

This invention relates to a blanket for covering it least a portion of the body of a human, or other animal, in order to bath the body portion in a conditioned gas. More specifically, the present invention is related to an inflatable thermal blanket having air flow channels for directing a conditioned gas, such as, for example, heated air, to a selected portion of the body of a user and preventing the conditioned gas from being directed at other portions of the body.

2. Description of the Related Art

Inflatable thermal blankets which are used to communicate a conditioned gas, such as heated or cooled air, to a patient are known in the art. Such thermal blankets typically have an inflatable portion provided with an inlet port for placing the inflatable portion in fluid communication with a source of pressurized, conditioned gas such that the inflatable portion can be selectively inflated. The inflatable portion generally has an inner surface which is gas pervious, or which is otherwise adapted to communicate the conditioned gas used to inflate the blanket to the user. Such thermal blankets are often used to treat conditions such as hypothermia, or used to reduce the body temperature of a user in circumstances where the body temperature is inappropriately high. For example, where a patient is being treated for hypothermia, at least a portion of the patient's body is covered with the thermal blanket, and warm air is pumped into the inflatable portion. The warm air used to inflate the inflatable portion is thereafter communicated through the inner surface of the inflatable portion so as to bath the body portion covered by the blanket in warm air. Examples of such thermal blankets are disclosed in U.S. Pat. Nos. 5,184,612; 5,304,213; and 5,324,320.

Whereas prior art thermal blankets serve to deliver conditioned air to a patient, the temperature of the air being communicated through the inner surface of the inflatable portion, and the surface temperature of the inner surface, can vary greatly over the area of the inner surface. For example, if heated air is pumped into the inflatable portion through the inlet port, the air within the blanket near the inlet port tends to be substantially higher in temperature than the air within the blanket which is remote from the inlet port. Accordingly, the inner surface of the blanket proximate the inlet port, and the air communicated to the patient through the inner surface of the blanket proximate the inlet port, can be uncomfortably, or damagingly, hot when the blanket is otherwise communicating air of the desired temperature to the patient. Whereas the temperature of the air entering the inlet port can be reduced to avoid uncomfortable, or damaging, hot spots near the inlet port, such a reduction of temperature can compromise the overall effectiveness of the thermal blanket.

BRIEF SUMMARY OF THE INVENTION

The present invention provides an inflatable thermal blanket for providing a conditioned gas, such as, for example, heated air, to at least a portion of the body of a human or other animal. The thermal blanket includes an inflatable portion for receiving the conditioned gas under pressure and for being positioned over at least a portion of the body of the user. The inflatable portion is defined by a base sheet which is fabricated of a gas pervious material, or which is otherwise adapted for communicating the conditioned gas to a portion of the body, and by an outer sheet which is substantially gas impervious. The inflatable portion also includes an inlet port for placing the inflatable portion in fluid communication with a source of conditioned gas. The inflatable portion is constructed so as to direct the conditioned gas along defined paths inside the inflatable portion. The defined paths are channels formed by joining the base sheet and outer sheet.

Another embodiment provides an inflatable portion that also includes a barrier sheet that is positioned adjacent the base sheet and which prevents the conditioned gas from passing through that portion of the base sheet so protected.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
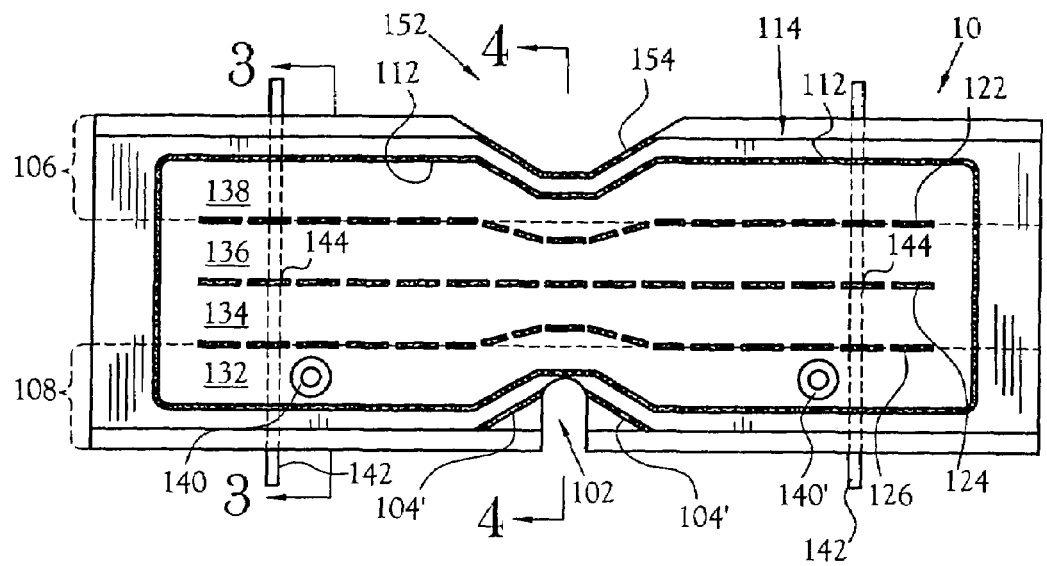
FIG. 1 is a plan view of one embodiment of a therapy blanket.
Figure 2:
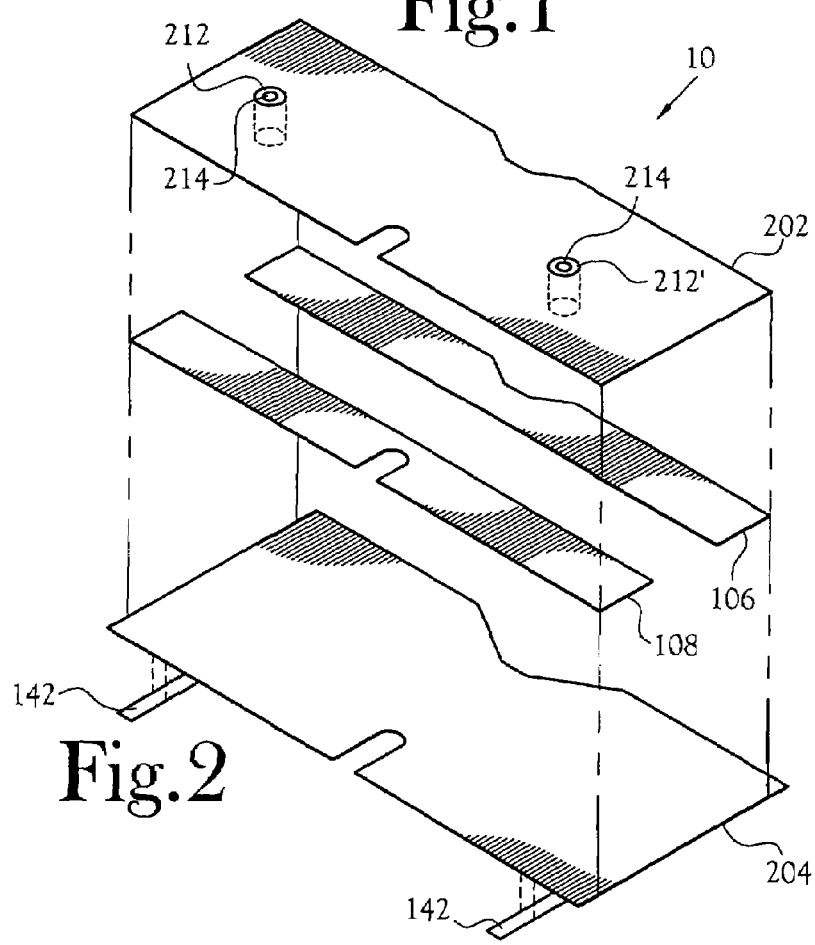
FIG. 2 is an exploded, perspective view of the therapy blanket.
Figure 5:
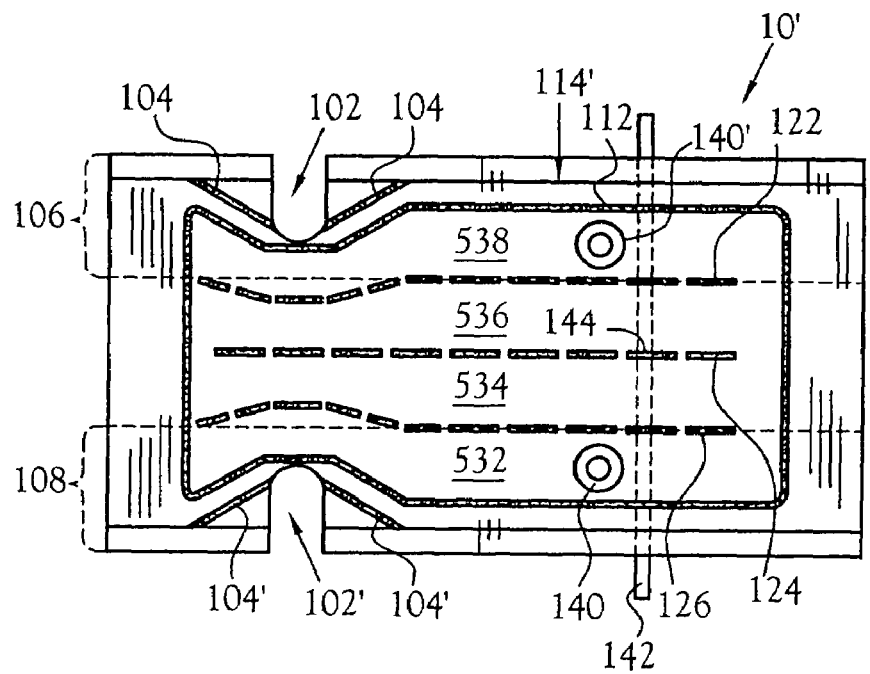
FIG. 5 is a plan view of another embodiment of a therapy blanket.
Figure 6:
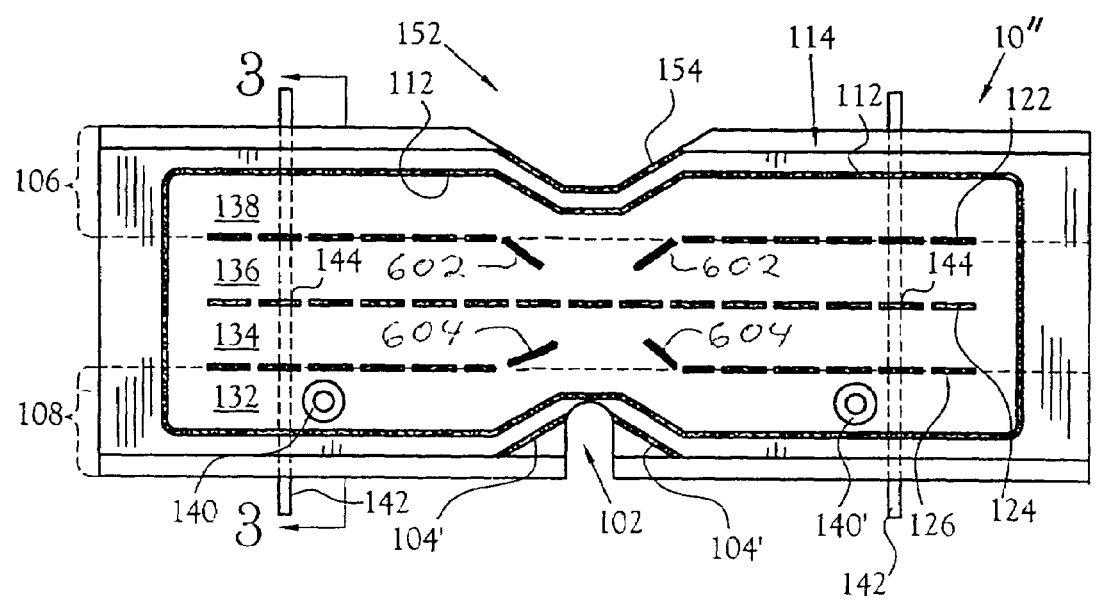
FIG. 6 is a plan view of another embodiment of the therapy blanket.

An inflatable thermal blanket in accordance with the present invention is illustrated generally at 10 in FIGS. 1 and 2, generally at 10' in FIG. 5, and generally at 10" in FIG. 6. The thermal blanket 10, 10', 10" is designed to cover at least a portion of the body of a human, or other animal, and to bath at least a portion of such body with a conditioned gas, such as thermally conditioned air. The thermal blanket 10, 10', 10" is particularly useful in bathing a body portion in air which has been heated to a temperature above normal body temperature in order to treat conditions such as hypothermia. However, it will be understood that gaseous fluids other than air can be used, and in certain applications the gaseous fluid utilized may be delivered to the body portion at a temperature which is at, or lower than, normal body temperature, as in the case where the existing body temperature is abnormally high and cooling is desired.

FIG. 1 illustrates a thermal blanket 10 for covering the torso and extended arms of a human. The blanket 10 is rectangular and includes an inflatable portion 114 surrounded by a seam 112, which joins the sheets forming the blanket 10. The blanket 10 extends beyond the inflatable portion 114 so as to drape over the patient in order to help retain the conditioned gas communicated to the patient.

Inside the inflatable portion are air flow channels 132, 134, 136, 138, which are formed by the outside seam 112 and inside seams 122, 124, 126. In the illustrated embodiment, the inside seams 122, 124, 126 are formed as a series of seam segments. The space between the seam segments aids in folding the blanket 10 because the seams stiffen the material forming the blanket 10, making the blanket 10 stiffer, and the space between the seams remains as flexible as the original materials forming the blanket 10. The space between the seam segments is short enough and the material is stiff enough that an appreciable amount of air does not cross from channel to channel through the seam segments.

In the illustrated embodiment, the blanket 10 is designed to accommodate the neck of a patient in one slot 102. The neck slot 102, in the illustrated embodiment, is a slot with parallel sides and a rounded end. Those skilled in the art will recognize that other opening shapes for the neck slot 102 can be used without departing from the spirit and scope of the present invention. With the slot 102 positioned around the neck of the patient, either of the inlet ports 140, 140' are available for connecting a blower for inflating the blanket 10. Opposite the neck slot 102 is a v-shaped notch, or cut-out, 152, which is adapted to fit about the chest or torso of the patient. The blanket 10 is taped to the chest or torso of the patient by applying tape to seam 154 surrounding the notch 152. Those skilled in the art will recognize that the shape of the torso notch 152 can vary without departing from the spirit and scope of the present invention. The neck slot 102 and the torso notch 152 lie substantially on the longitudinal axis of the patient.

Pressurized, conditioned air is introduced to the blanket 10 through either port 140, 140'. The pressurized air fills the first channel 132, which inflates. The air in the first channel 132 is directed to the ends of the channel 132, where the air enters and inflates the other channels 134, 136, 138. The inside seams 122, 126 and the outside seam 112 form constricting channels 132, 134, 136, 138 in the region between the neck slot 102 and the chest notch 152. When inflated, this portion of the channels 132, 134, 136, 138 form smaller diameter tubes, or channels, than the distal ends of the channels 132, 134, 136, 138. The reduced diameter portion of the channels 132, 134, 136, 138 prevents the blanket 10 from bunching or deforming where it covers the torso of the patient. In the illustrated embodiment, the cross-section of each of the channels 132, 134, 136, 138 is approximately the same size, thereby ensuring that the air flow is not restricted by any one channel 132, 134, 136, 138.

The illustrated embodiment shows two straps 142 attached at a center-point 144 under the thermal blanket 10. The straps 142 are used to secure the blanket 10 to the extended arms of a patient.

FIG. 2 is an exploded view of the embodiment of the thermal blanket 10 illustrated in FIG. 1. The base sheet 204 is a substantially rectangular sheet fabricated of a substantially air permeable material, such as, for example, a natural or synthetic non-woven material through which air under pressure can be communicated. Whereas synthetic materials such as, for example, polyester, can be used, the use of a cellulose or paper based material has advantages where a single use, disposable thermal blanket 10 is desired. In another embodiment, the base sheet 204 is fabricated of an air impermeable material that is provided with openings through which gas can pass. In still another embodiment, the base sheet 204 is fabricated of a material that is air permeable in selected areas and otherwise air impermeable. The top sheet 202 is a substantially rectangular sheet fabricated out of a substantially air impermeable material, such as, for example, a cellulose based sheet material coated with a film of polyethylene or polypropylene. Between the base sheet 204 and the top sheet 202 are barrier sheets 106, 108, which are impervious to gas. The barrier sheets 106, 108 are substantially rectangular sheets fabricated out of an air impermeable material, such as, for example, polyethylene or polypropylene.

Reinforcing collars 212, 212' for the inlet ports 140, 140' have openings 214, 214' for receiving the end of the supply hose from a blower. The collars 212, 212' are secured to the top sheet 202 with an adhesive. The openings 214, 214' are approximately 2¼ inches in diameter. In one embodiment, the top sheet 202 does not have a corresponding opening in the top sheet 202 corresponding to at least one of the 212, 212'. When the thermal blanket 10 is used, the portion of the top sheet 202 within the opening 214, 214' is torn to allow the insertion of the end of the hose. In another embodiment, the area to be torn is scored to aid in tearing.

Below the base sheet 204 are two straps 142. The straps are secured to the base sheet at a center-point 144 with an adhesive. In one embodiment, the straps 142 are approximately 1 inch wide by 50 inches long. Those skilled in the art will recognize that the straps 142 can be fabricated of any flat, pliable material without departing from the spirit and scope of the present invention. In various embodiments, the straps 142 are fabricated of the same material as the base sheet 204 or the top sheet 202.

Each of the sheets 202, 204, 106, 108 has a notch, or cutout portion, 102, 102' which is sized to fit around the neck and chin of the patient. The base sheet 204 and the top sheet 202 are joined at a seam 112, which defines the inflatable portion 114. The sheets 202, 204, 106, 108 are also secured together by a plurality of intermittent seams 122, 124, 126. The plurality of intermittent seams 122, 124, 126, serve the function of forming channels 132, 134, 136, 138 and of directing the conditioned gas within the inflatable portion 114.

The barrier sheets 106, 108 define an area in which the air pervious base sheet 204 does not pass air to the patient. In the illustrated embodiment the barrier sheets 106, 108 are the same length as the base sheet 204, which facilitates manufacture of the thermal blanket 10, and it will be recognized that barrier sheets 106, 108, which extend only the length of the inflatable portion 114, or along a portion of the length of the inflatable portion 114, can be used. Similarly, in order to facilitate manufacture, the top sheet 202 extends the length of the base sheet 204, but it will be recognized that the top sheet 202 need only be of sufficient length to form the outer wall of the inflatable portion 114.

The base sheet 204, the top sheet 202, and the barrier sheets 106, 108 are heat bonded together within the inflated portion 114 of the blanket 10 at intermittent seams 122, 124, 126. The base sheet 204 and the top sheet 202 are heat bonded together to form the inflated portion 114 of the blanket 10 at seam 112. The seams 112, 122, 124, 126 are formed, in one embodiment, by heat bonding. Those skilled in the art will recognize that various adhesive or other bonding methods can be used without departing from the spirit or scope of the present invention.

Figure 3:
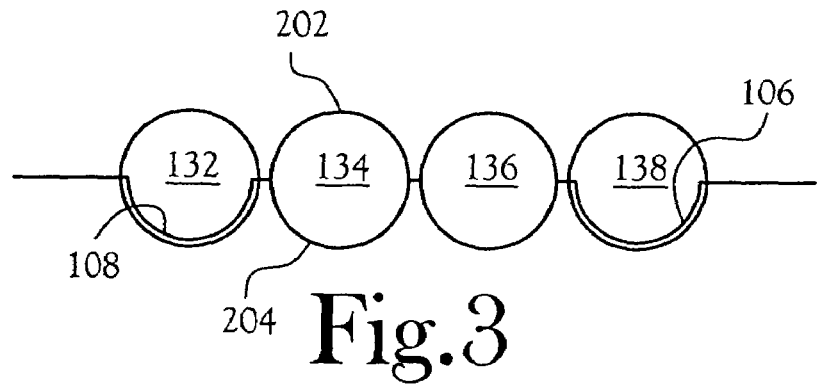
FIG. 3 is a cross-sectional view of the blanket of FIG. 1.

FIG. 3 illustrates a cross-section of an inflated blanket 10. The air flow channels 132, 134, 136, 138 form tubes as the air forced into the inflatable portion 114 forces the top sheet 202 and the base sheet 204 away from each other. The barrier sheets 108, 106 are forced against the base sheet 204 by the air pressure, thereby preventing the air from exhausting from the outside channels 132, 138.

Figure 4:
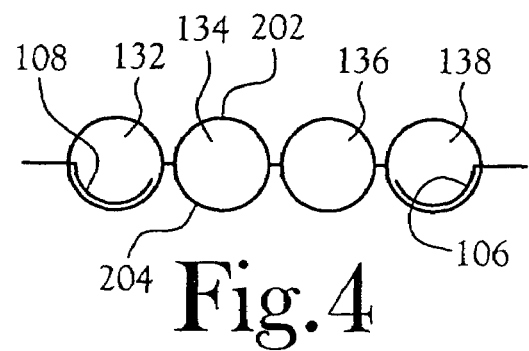
FIG. 4 is a second cross-sectional view of the blanket of FIG. 1.

FIG. 4 illustrates a cross-section of an inflated blanket 10 in the torso area. The air flow channels 132, 134, 136, 138 form tubes as the air forced into the inflatable portion 114 forces the top sheet 202 and the base sheet 204 away from each other. Because the outside seam 112 and the intermittent seams 122, 126 are closer together, the air flow channels 132, 134, 136, 138 form smaller diameter tubes over the patient's torso. In the illustrated embodiment, the barrier sheets 108, 106 do not fully cover the air permeable portion of the air flow channels 132, 138. By making all four tubes smaller over the torso, the blanket 10 does not become distorted or tent over in the region over the torso. As the blanket 10 is inflated, the blanket 10 maintains its substantially flat shape.

Each of the air flow channels 132, 134, 136, 138 illustrated in FIGS. 3 and 4 have a diameter when inflated because the material of the inflatable portion 114 balloons with each of the air flow channels 132, 134, 136, 138 assuming a substantially tubular shape. The diameter of the air flow channels 132, 134, 136, 138 at a location away from the where the therapy blanket 10, 10', 10" (illustrated in FIG. 3)covers the patient's torso are larger than the inflated diameter of the air flow channels 132, 134, 136, 138 at a location between the neck cutout portion 102 and the other neck cutout portion 102' or the chest notch 152 (illustrated in FIG. 4).

FIG. 5 illustrates another embodiment of a therapy blanket 10' for covering a torso and one arm of a patient. The illustrated embodiment of the one-arm blanket 10' has two neck slots 102, 102' and two inlet ports 140, 140'. This embodiment offers the greatest flexibility for positioning the blanket 10' on a patient and connecting the blower to the inlet 140, 140'.

The one-arm blanket 10' has four air flow channels 532, 534, 536, 538 in which air is directed within the inflatable portion 114. As conditioned air is introduced into the port 140, the adjacent channel 532 inflates. The air flows to the ends of the channel 532, where the air enters the other channels 534, 536, 538. In the illustrated embodiment, the air has less restriction for entering the other channels 534, 536, 538 at the end located away from the neck slots 102, 102'. In another embodiment, both ends of the channels 532, 534, 536, 538 are open to air flowing between the channels 532, 534, 536, 538.

The illustrated embodiment shows a strap 142 attached at a center-point 144 under the thermal blanket 10. The strap 142 is used to secure the blanket 10 to the extended arm of a patient.

FIG. 6 illustrates another embodiment of a therapy blanket 10" for covering the torso and extended arms of a human. The embodiment of the therapy blanket 10" illustrated in FIG. 6 differs from the embodiment of the therapy blanket 10 illustrated in FIG. 1 in the configuration of the inside seams 122, 124, 126. The seams 122, 126 have a discontinuous section where the seams 122, 126 are broken in the middle with a portion 602, 604 of the seam 122, 126 projecting into the channel 136, 134, respectively. In this embodiment, the channels 136, 138 and the channels 132, 134 are connected, or communicate, at their distal ends and at the center of the channels. In the illustrated embodiment, the seam portions 602, 604 are positioned obliquely to the air flow channels 132, 134, 136, 138. In the illustrated embodiment, the seam portions 602, 604 are angled toward the center of the inflatable chamber 112 and add stability to the therapy blanket 10" and aid in maintaining air flow under low air pressure conditions.

The thermal blanket 10, 10', 10" includes various functions. The function of restricting a volume of the inflatable chamber 112 adjacent a line between the neck slot 102 and the torso notch 152 is implemented, in one embodiment, by the air channels 132, 134, 136, 138 having a reduced diameter in the area between the neck slot 102 and the torso slot 152, in one embodiment, and between the two neck slots 102, 102' in another embodiment. In another embodiment, the function of restricting a volume of the inflatable chamber 112 is accomplished as illustrated in FIG. 6 wherein the seams 122, 126 have a discontinuous section between the seam portions 602, 604 located between the neck cutout 102 and the other neck cutout portion 102' or the chest notch 152.

The function of preventing the conditioned air from being discharged from a selected portion of the base sheet 204 is implemented, in one embodiment, by one or both of the barrier sheets 106, 108 sandwiched between the top sheet 202 and the base sheet 204. The barrier sheet 106, 108 prevents air from exhausting through the base sheet 204.

The function of attaching the therapy blanket 10, 10', 10" to the patient is implemented, in one embodiment, by the neck slot 102 and the torso notch 153, which are adapted to secure the therapy blanket 10, 10', 10" to the patient, for example, by taping the blanket 10, 10', 10" to the patient or cover over the patient. In another embodiment, the function of attaching the therapy blanket 10, 10', 10" is implemented by a strap 142 adapted to be tied to an extended arm of the patient.

From the foregoing description, it will be recognized by those skilled in the art that a therapy blanket with unique features has been provided. The blanket covers the torso and at least one extended arm of a patient. The therapy blanket has an inflatable portion that includes air channels with a constriction in the area where the blanket covers the torso of the patient; thereby reducing, if not eliminating, bunching of the blanket.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

The invention claimed is:

1. A therapy blanket for providing conditioned air to a patient, said therapy blanket comprising:
   a top sheet of a first air impermeable material;
   a base sheet adapted to pass the conditioned air, said top sheet and said base sheet joined by a continuous seam forming an inflatable chamber, said top sheet and said bottom sheet having a neck slot and a torso notch for positioning said therapy blanket over the patient, said neck slot and said torso notch located on opposite sides of said therapy blanket;
   a pair of air channels formed by joining said top sheet and said base sheet at a first channel seam, said first channel seam positioned transverse to a line between said neck slot and said torso notch, said pair of air channels each having an inflated cross-sectional area, said inflated cross-sectional area being smaller at said pair of air channels where said pair of air channels crosses said line between said neck slot and said torso notch;

an inlet port for providing the conditioned air to said inflatable chamber; and at least one barrier sheet of a second air impermeable material, said at least one barrier sheet sandwiched between said top sheet and said base sheet whereby air is prevented from being discharged from a selected portion of said base sheet, said at least one barrier sheet secured between said top sheet and said base by at least one of said continuous seam and said channel seam.

2. The therapy blanket of claim 1 further including at least one strap attached to said base sheet and positioned parallel to said line between said neck slot and said torso notch whereby said at least one strap is adapted to fasten said therapy blanket to an arm of the patient.

3. The therapy blanket of claim 1 wherein said inflatable chamber extends from said line between said neck slot and said torso notch a distance to substantially cover an extended arm of the patient.

4. The therapy blanket of claim 1 wherein said neck slot and said torso notch are substantially the same shape whereby said torso notch is suitable for positioning about a neck of said patient.

5. The therapy blanket of claim 1 wherein said inflatable chamber extends on each side of said line between said neck slot and said torso notch a distance to cover each extended arm of the patient.

6. The therapy blanket of claim 1 wherein said first channel seam has a discontinuous section located about said line between said neck slot and said torso notch whereby said pair of air channels communicate through said discontinuous section, said discontinuous section being bounded by a pair of seam sections positioned obliquely to said pair of air channels.

7. The therapy blanket of claim 1 further including a second pair of air channels formed by joining said top sheet and said base sheet at a second channel seam, said second channel seam positioned substantially parallel to said first channel seam.

8. The therapy blanket of claim 7 wherein said second channel seam has a discontinuous section located about said line between said neck slot and said torso notch whereby said second pair of air channels communicate through said discontinuous section, said discontinuous section being bounded by a pair of seam sections positioned obliquely to said second pair of air channels.

9. A therapy blanket for providing conditioned air to a patient, said therapy blanket comprising:

a neck slot for positioning said therapy blanket about the patient; and an inflatable chamber having a generally rectangular shape, said inflatable chamber comprising:

an exhaust surface for releasing the conditioned air toward the patient;

an inlet port for receiving the conditioned air; and a plurality of air channels, each of said plurality of air channels being substantially parallel with others of said plurality of air channels, said plurality of air channels being substantially perpendicular to a line extending through said neck slot and generally following a longitudinal axis of the patient, said inflatable chamber having a first cross-sectional area where said plurality of air channels cross a plane perpendicular to said plurality of air channels and passing through said neck slot, said inflatable chamber having a second cross-sectional area at a position between said plane and a distal end of each of said plurality of air channels, said first cross-sectional area being smaller than said second cross-sectional area.

10. The therapy blanket of claim 9 wherein each of said plurality of air channels having a first diameter where said plurality of air channels cross a plane perpendicular to said plurality of air channels and passing through said neck slot, each of said plurality of air channels having a second diameter at a position between said plane and a distal end of each of said plurality of air channels, said first diameter being smaller than said second diameter.

11. The therapy blanket of claim 9 further including a barrier sheet disposed inside said inflatable chamber, said barrier sheet positioned to block air flow from a portion of said exhaust surface.

12. The therapy blanket of claim 9 further including a means for preventing the conditioned air from being discharged from a selected portion of said base sheet.

13. The therapy blanket of claim 9 further including a torso notch opposite said neck slot, said torso notch adapted to attach said therapy blanket to the patient.

14. The therapy blanket of claim 9 further including a means for attaching said therapy blanket to the patient.

15. The therapy blanket of claim 9 further including at least one strap attached to said base sheet and positioned parallel to said line between said neck slot and said torso notch whereby said at least one strap is adapted to fasten said therapy blanket to an arm of the patient.

16. The therapy blanket of claim 9 wherein said inflatable chamber extends from said line between said neck slot and said torso notch a distance to substantially cover an extended arm of the patient.

17. The therapy blanket of claim 9 wherein said neck slot and said torso notch are substantially the same shape whereby said torso notch is suitable for positioning about a neck of said patient.

18. The therapy blanket of claim 9 wherein said inflatable chamber extends on each side of said line between said neck slot and said torso notch a distance to cover each extended arm of the patient.

19. A therapy blanket for providing conditioned air to a patient, said therapy blanket comprising:

a top sheet of a first air impermeable material;

a base sheet adapted to pass the conditioned air, said top sheet and said base sheet joined by a continuous seam forming an inflatable chamber, said top sheet and said bottom sheet having a neck slot and a torso notch for positioning said therapy blanket over the patient, said neck slot and said torso notch located on opposite sides of said therapy blanket;

a pair of air channels formed by joining said top sheet and said base sheet joined at a channel seam, said channel seam positioned transverse to a line between said neck slot and said torso notch;

an inlet port for providing the conditioned air to said inflatable chamber; and a means for restricting a volume of said inflatable chamber adjacent said line between said neck slot and said torso notch.

20. The therapy blanket of claim 19 further including a means for preventing the conditioned air from being discharged from a selected portion of said base sheet.

* * * * *